United States Patent
Kalvins et al.

(10) Patent No.: US 10,351,534 B2
(45) Date of Patent: Jul. 16, 2019

(54) USE OF 3-CARBOXY-N-ETHYL-N,N-DIMETHYLPROPAN-1-AMINIUM SALTS IN THE TREATMENT OF CARDIOVASCULAR DISEASE

(71) Applicant: JSC GRINDEKS, Riga (LV)

(72) Inventors: Ivars Kalvins, Ikskile (LV); Edgars Liepins, Riga (LV); Einars Loza, Jurmala (LV); Maija Dambrova, Riga (LV); Ilmars Stonans, Riga (LV); Daina Lola, Riga (LV); Janis Kuka, Jelgava (LV); Osvalds Pugovics, Riga (LV); Reinis Vilksersts, Riga (LV); Solveiga Grinberga, Salaspils (LV)

(73) Assignee: JSC GRINDEKS, Riga (LV)

( * ) Notice: Subject to any disclaimer, the term of this patent is extended or adjusted under 35 U.S.C. 154(b) by 0 days.

(21) Appl. No.: 15/828,660

(22) Filed: Dec. 1, 2017

(65) Prior Publication Data

US 2018/0079728 A1    Mar. 22, 2018

Related U.S. Application Data

(63) Continuation of application No. 14/113,709, filed as application No. PCT/EP2012/057806 on Apr. 27, 2012, now abandoned.

(30) Foreign Application Priority Data

| Apr. 27, 2011 | (EP) | 11163839 |
| Apr. 27, 2011 | (EP) | 11163840 |
| Apr. 27, 2011 | (EP) | 11163841 |
| Apr. 27, 2011 | (EP) | 11163871 |
| Apr. 27, 2011 | (EP) | 11163872 |

(51) Int. Cl.
*C07C 229/12* (2006.01)
*C07C 227/18* (2006.01)
*C07D 239/10* (2006.01)
*C07C 55/10* (2006.01)
*C07C 57/15* (2006.01)
*C07C 227/08* (2006.01)
*C07D 239/557* (2006.01)
*C07C 69/157* (2006.01)
*C07C 225/06* (2006.01)

(52) U.S. Cl.
CPC ........... *C07D 239/10* (2013.01); *C07C 55/10* (2013.01); *C07C 57/15* (2013.01); *C07C 69/157* (2013.01); *C07C 225/06* (2013.01); *C07C 227/08* (2013.01); *C07C 227/18* (2013.01); *C07C 229/12* (2013.01); *C07D 239/557* (2013.01)

(58) Field of Classification Search
CPC .... A61K 31/19; A61K 31/685; A61K 31/167; C07C 51/412; C07C 229/12
See application file for complete search history.

(56) References Cited

U.S. PATENT DOCUMENTS

| 5,017,611 A | 5/1991 | Bremanis et al. ............ 514/551 |
| 5,965,615 A | 10/1999 | Kalvinsh et al. |

FOREIGN PATENT DOCUMENTS

| EP | 1103259 A1 * | 5/2001 | ........... A61K 31/205 |
| EP | 2070529 | 6/2009 | |
| WO | WO 97/06794 | 2/1997 | |
| WO | WO 97/06795 | 2/1997 | |
| WO | WO 2009/071586 A2 | 6/2009 | |
| WO | WO 2010/149654 | 12/2010 | |
| WO | WO 2010/151095 | 12/2010 | |
| WO | WO 2011/048201 | 4/2011 | |

OTHER PUBLICATIONS

EP 1,103,259 A1 published May 2001, machine translation obtained from EPO website Aug. 27, 2014 (Year: 2001).*
International Search Report With Written Opinion for PCT/EP2012/057806 dated Aug. 21, 2012.
Lindstedt, et al., Journal of Biological Chemistry, 1970, 245, 4178-4186.
Liepinsh, et al., British Journal of Pharmacology, 2015, 172, 1319-1332.
Liepinsh, et al., Journal of Cardiovascular Pharmacology, 2006, 48, 314-319.

* cited by examiner

*Primary Examiner* — Marcos L Sznaidman
*Assistant Examiner* — Rayna Rodriguez
(74) *Attorney, Agent, or Firm* — Hueschen and Sage

(57) ABSTRACT

Salts of 3-carboxy-N-ethyl-N,N-dimethylpropan-1-aminium, method of preparation thereof and use in the treatment of cardiovascular disease.

6 Claims, No Drawings

USE OF 3-CARBOXY-N-ETHYL-N,N-DIMETHYLPROPAN-1-AMINIUM SALTS IN THE TREATMENT OF CARDIOVASCULAR DISEASE

TECHNICAL FIELD

The present invention relates to new compound 3-carboxy-N-ethyl-N,N-dimethylpropan-1-aminium salts, and to a method of preparation thereof (compound of formula 4)

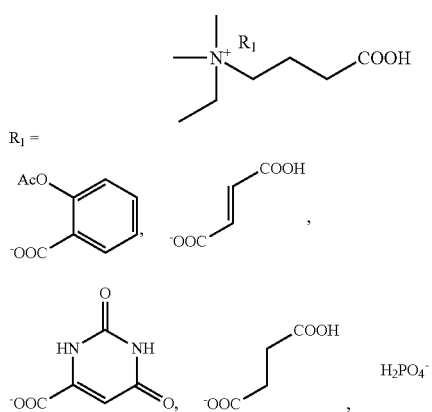

The present invention relates also to use of 3-carboxy-N-ethyl-N,N-dimethylpropan-1-aminium salts in the treatment of cardiovascular disease.

BACKGROUND ART

Cardiovascular diseases (CVDs) are a group of disorders of the heart and blood vessels.

An estimated 16.7 million—or 29.2% of total global deaths—result from the various forms of cardiovascular disease (CVD).

Myocardial infarction (heart attack) is a serious result of coronary artery disease. Myocardial infarction (MI) is the irreversible necrosis of heart muscle secondary to prolonged ischemia. A heart attack or myocardial infarction is a medical emergency in which the supply of blood to the heart is suddenly and severely reduced or cut off, causing the muscle to die from lack of oxygen. More than 1.1 million people experience a heart attack (myocardial infarction) each year, and for many of them, the heart attack is their first symptom of coronary artery disease. A heart attack may be severe enough to cause death or it may be silent. As many as one out of every five people have only mild symptoms or none at all, and the heart attack may only be discovered by routine electrocardiography done some time later.

A heart attack (myocardial infarction) is usually caused by a blood clot that blocks an artery of the heart. The artery has often already been narrowed by fatty deposits on its walls. These deposits can tear or break open, reducing the flow of blood and releasing substances that make the platelets of the blood sticky and more likely to form clots. Sometimes a clot forms inside the heart itself, then breaks away and gets stuck in an artery that feeds the heart. A spasm in one of these arteries causes the blood flow to stop.

γ-Butyrobetaine, from which the mammalian organism synthesises carnitine, was primarily characterised as a toxic substance which accelerates respiration, causes salivation and lacrimation, pupil dilation, vasoconstriction and heart stop in diastole LINNEWEH, W. Gamma-Butyrobetain, Crotonbetain und Carnitin im tierischen Stoffwechsel. *Hoppe-Seylers Zeitschrift für physiologische Chemie.* 1929, vol. 181, p. 42-53. At the same time, in later papers other authors ascertained that γ-butyrobetaine is extremely low toxic (LD50>7000 mg/kg, s.c.) ROTZSCH, W. Iber die Toxizitat des Carnitins und einiger verwandter Stoffe. *Acta biol. med. germ.* 1959, vol. 3, p. 28-36.

In the literature data on nonsubstituted γ-butyrobetaine cardiovascular effects are missed, thought it was reported HOSEIN, E. A. Pharmacological actions of γ-butyrobetaine. *Nature.* 1959, vol. 183, p. 328-329. that γ-butyrobetaine is a substance similar to acetyl choline with a prolonged action. However, later the same authors reported that by an error the experiments involved, instead of γ-butyrobetaine, its methyl ester which in fact possesses cholinergic properties. Contrary to the former γ-butyrobetaine was characterised as a pharmacologically inert substance HOSEIN, E. A. Isolation and probable functions of betaine esters in brain metabolism. *Nature.* 1960, vol. 187, p. 321-322.

As structurally related compounds to 3-carboxy-N-ethyl-N,N-dimethylpropan-1-aminium salts are disclosed in:
- GB 1238868 A 14 Jul. 1971 were disclosed betaines, such as 4-trimethylammoniobutanoate, used for polymers. However no pharmacological properties of these betaines weren't presented;
- U.S. Pat. No. 5,973,026 A (XEROX CORP) 26 Oct. 1999 were disclosed 4-trimethylammoniobutanoate and 3-[diethyl(methyl)ammonio]propionate for using for ink compositions;
- LLOYD ANDREW, et al. A comparison of glycine, sarcosine, N,N-dimethylglycine, glycinebetaine and N-modified betaines as liposome cryoprotectants. *Journal of pharmacy and pharmacology.* 1992, vol. 44, no. 6, p. 507-511 disclosed 2-[ethyl(dimethyl)ammonio]acetate used as cryoprotectants for liposomes;
- DAVID B., THOMAS, et al. Synthesis, Characterization, and Aqueous Solution Behavior of Electrolyte- and pH-Responsive Carboxybetaine-Containing Cyclocopolymers. *Macromolecules.* 2003, vol. 36, no. 26, p. 9710-9715 disclose 4-[diallyl(methyl)ammonio]butanoate and its synthesis starting from N,N-diallyl-N-methylaminiom and ethyl 4-bromobutanoate. The free acids is obtained from the ester in a second step using Amberlite ion exchange resin. The product is used as intermediate to synthesise polymers;
- *Prelog V.* 1930, vol. 2, p. 712-722 disclosed the synthesis of 4-trimethylammoniobutanoate starting from 4-dimethylammoniobutanoate and methyliodide;
- 4-Trimethylammoniobutanoate and its synthesis starting from trimethylamine and ethyl 4-bromobutanoate was described JP 2009096766 A (KONAN GAKUEN) 7 Jul. 2009. The free acid is obtained from the ester in a second step using Amberlite ion exchange resin;
- WO 2008/055843 A (KALVINSH IVARS; CHERNOBROVIJS ALEKSANDRS; VARACHEVA LARISA; PUGOVICHS OSVALDS) 15 May 2008 was described 4-trimethylammoniobutanoate and synthesis, which started from the corresponding ester and using KOH-solution;
- CA 2508094 A (VIVIER CANADA INC) 20 Nov. 2006 was disclosed betaines, such as 4-trimethylammoniobutanoate, for use as medicament for accelerating collagen synthesis;

U.S. Pat. No. 5,965,615 A (TAIHO PHARMACEUTICAL CO LTD; VALSTS ZINATNISKA IESTADE BEZP) 12 Oct. 1999 was disclosed 4-trimethylammoniobutanoate as a medicament for the treatment of myocardial metabolic disorder, the same compound was disclosed in US 2007191381 A (CONCERT PHARMACEUTICALS INC) 16 Aug. 2007 for treatment of myocardial infarction.

3-(2,2,2-Trimethylhydrazinium) propionate dihydrate is known as compound with cardioprotective properties (this substance being known under its International Nonproprietary Name of Meldonium). 3-(2,2,2-Trimethylhydrazinium) propionate is disclosed in U.S. Pat. No. 4,481,218 (INST ORGANICHESKOGO SINTEZA) 6 Nov. 1984 as well in U.S. Pat. No. 4,451,485 A (INSTITU ORCH SINTEZA AKADEMII) 29 May 1984.

It is well known that 3-(2,2,2-trimethylhydrazinium) propionate as dihydrate is widely used for controlling carnitine and gamma-butyrobetaine concentration ratio and consequently the speed of fatty acid beta-oxidation in the body DAMBROVA M., LIEPINSH E., KALVINSH I. I. Mildronate: cardioprotective action through carnitine-lowering effect. *Trends in Cardiovascular Medicine*, 2002, vol. 12, no. 6, p. 275-279.

Due to these properties, Meldonium is extensively applied in medicine as an anti-ischemic, stress-protective and cardioprotective drug in treating various cardiovascular diseases and other pathologies involving tissue ischemia KARPOV R. S., KOSHELSKAYA O. A., VRUBLEVSKY A. V., SOKOLOV A. A., TEPLYAKOV A. T., SKARDA I., DZERVE V., KLINTSARE D., VITOLS A., KALNINS U., KALVINSH I., MATVEYA L., URBANE D. Clinical Efficacy and Safety of Mildronate in Patients With Ischemic Heart Disease and Chronic Heart Failure. *Kardiologiya*. 2000, no. 6, p. 69-74. In the treatment of cardiovascular diseases the mechanism of action of 3-(2,2,2-trimethylhydrazinium)propionate based on limitation of carnitine biosynthesis rate and related long-chain fatty acid transport limitation through mitochondria membranes SIMKHOVICH B. Z., SHUTENKO Z. V., MEIRENA D. V., KHAGI K. B., MEZHAPUKE R. J., MOLODCHINA T. N., KALVINS I. J., LUKEVICS E. 3-(2,2,2,-Trimethylhydrazinium)propionate (THP)—a novel gamma-butyrobetaine hydroxylase inhibitor with cardioprotective properties. *Biochemical Pharmacology*. 1988, vol. 37, p. 195-202., KIRIMOTO T., ASAKA N., NAKANO M., TAJIMA K., MIYAKE H., MATSUURA N. Beneficial effects of MET-88, a γ-butyrobetaine hydroxylase inhibitor in rats with heart failure following myocardial infarction. *European Journal of Pharmacology*. 2000, vol. 395, no. 3, p. 217-224.

SUMMARY OF INVENTION

As it was known what Meldonium dihydrate has cardioprotective effect; however there are no data that γ-butyrobetaine itself has pronounced cardioprotective effect. In the patent EP 0845986 B (KALVINSH IVARS, VEVERIS MARIS) 2 Apr. 2003 is disclosed pharmaceutical composition of Meldonium dihydrate and γ-butyrobetaine for use in the treatment of cardiovascular diseases.

An object of the present invention is to provide a compound, which has pronounced cardioprotective effect.

The above-mentioned object is attained by providing new compounds 3-carboxy-N-ethyl-N,N-dimethylpropan-1-aminium salts (compound of formula 4), which has similar structure to Meldonium or γ-butyrobetaine.

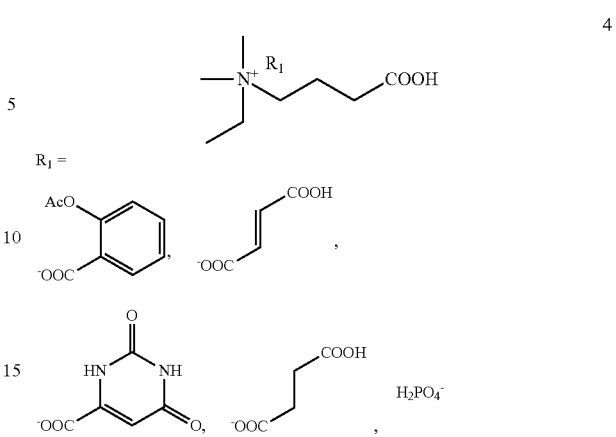

To our surprise 3-carboxy-N-ethyl-N,N-dimethylpropan-1-aminium salts posses pronounced cardioprotective effect and are more effective as Meldonium dihydrate in vivo myocardial infarction models, due to this property 3-carboxy-N-ethyl-N,N-dimethylpropan-1-aminium salts may be used in medicine. 3-Carboxy-N-ethyl-N,N-dimethylpropan-1-aminium salts can be use as a solution for injection.

The following object of the present invention is a method of preparation of said compound of formula 4.

There is disclosed process, which can be used in purpose to prepare target compound 3-carboxy-N-ethyl-N,N-dimethylpropan-1-aminium salts of formula 4, see scheme bellow.

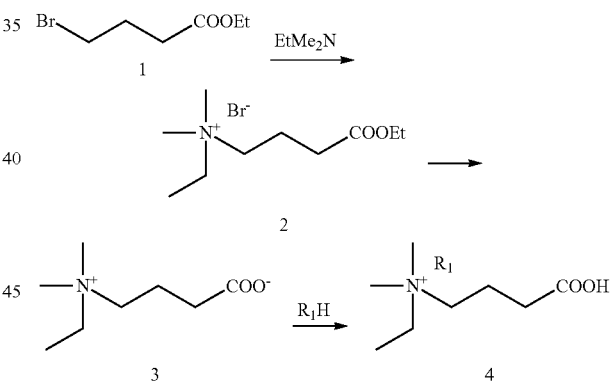

Process for preparing 3-carboxy-N-ethyl-N,N-dimethylpropan-1-aminium salt of formula 4 involves the following process steps:

a) adding N,N-dimethylethylamine to ethyl 4-bromobutanoate (1) in appropriate solvent to obtain 4-ethoxy-N-ethyl-N,N-dimethyl-4-oxo-1-butanaminium bromide (2);

b) passing 4-ethoxy-N-ethyl-N,N-dimethyl-4-oxo-1-butanaminium bromide (2) through ion exchange resin column to obtain 4-[ethyl(dimethyl)ammonio] butanoate (3);

c) adding acid which is selected from 2-(acetyloxy) benzoic acid (4 a) or (E)-butenedioic acid (4 b) or succinic acid (4 c) or 2,6-dioxo-1,2,3,6-tetrahydropyrimidine-4-carboxylic acid monohydrate (4 d) or phosphoric acid (4 e) to 4-[ethyl(dimethyl)ammonio]

butanoate (3) in appropriate solvent to obtain 3-carboxy-N-ethyl-N,N-dimethylpropan-1-aminium salt (4).

DESCRIPTION OF EMBODIMENTS

The present invention will be described in more detail by referring to the following non-limiting examples.

Preparation of 4-ethoxy-N-ethyl-N,N-dimethyl-4-oxo-1-butanaminium bromide (2)

Procedure A

To a solution of ethyl 4-bromobutanoate (1) (20.0 g, 102.5 mmol) in acetonitrile (70 ml) N,N-dimethylethylamine (15 ml, 139 mmol) was added and stirred at ambient temperature for 3 days. The reaction mixture was evaporated, the residue was triturated with acetone (50 ml), filtered, washed with ether, and dried to afford 26.051 g (94.8%) of the 4-ethoxy-N-ethyl-N,N-dimethyl-4-oxo-1-butanaminium bromide. LCMS (ESI$^+$, m/z): [M-Br$^-$]$^+$188, purity 98.9%.

$^1$H NMR (CDCl$_3$, HMDSO) δ: 1.26 (t, J=7.2 Hz, 3H); 1.44 (t, J=7.4 Hz, 3H); 2.00-2.11 (m, 2H); 2.52 (t, J=6.6 Hz, 2H); 3.40 (s, 6H); 3.64-3.73 (m, 2H); 3.69 (q, J=7.4 Hz, 2H); 4.14 (q, J=7.2 Hz, 2H).

Procedure B

To a solution of ethyl 4-bromobutanoate (1) (19.5 g, 100 mmol) in acetone (70 ml) N,N-dimethylethylamine (15 ml, 139 mmol) was added and stirred at ambient temperature for 3 days. The reaction mixture was filtered; the solid material was washed with an acetone, ether, and dried to afford 24.19 g (90.2%) of the title compound 2. The filtrate was evaporated; the residue (2.147 g) was triturated with ether and dried to give an extra batch (0.962 g, 3.6%) of the product 2 of the same quality as the main portion. The evaporation of the ether washings allowed recovering 0.956 g (4.9 mmol, 4.9%) of the starting material 1. 4-ethoxy-N-ethyl-N,N-dimethyl-4-oxo-1-butanaminium bromide: LCMS (ESI$^+$, m/z): [M-Br$^-$]$^+$188, purity 98.4%.

$^1$H NMR (CDCl$_3$, HMDSO) δ: 1.26 (t, J=7.2 Hz, 3H); 1.44 (t, J=7.4 Hz, 3H); 2.00-2.11 (m, 2H); 2.52 (t, J=6.6 Hz, 2H); 3.40 (s, 6H); 3.64-3.73 (m, 2H); 3.69 (q, J=7.4 Hz, 2H); 4.14 (q, J=7.2 Hz, 2H).

Preparation of 4-[ethyl(dimethyl)ammonio]butanoate (3)

A solution of 4-ethoxy-N-ethyl-N,N-dimethyl-4-oxo-1-butanaminium bromide (2) (12.00 g, 44.7 mmol) in water (10 ml) was passed through Amberlite® IRA-410 (OH) ion exchange resin column (250 ml) eluting slowly (ca. 10 drops/min) with ethanol (TLC control). The eluate was evaporated and the residue (12 g) was dissolved in water (50 ml). To this solution DOWEX® 50WX8 ion exchange resin (5 g) was added and stirred at ambient temperature for 0.5 h. The reaction mixture was filtered through celite (1 cm) and the eluate was evaporated. The residue was azeotropically dried with isopropanol, acetonitrile, and acetone. The obtained solid was triturated with acetone (10 ml) and the mixture was kept at 0° C. for 2 h. The precipitate was filtered and dried in vacuo over P$_2$O$_5$ to give 4.65 g (65%) of the 4-[ethyl(dimethyl)ammonio]butanoate (3).

(DMSO-d$_6$, HMDSO) δ: 1.24 (t, J=7.3 Hz, 3H); 1.66-1.76 (m, 2H); 1.81 (t, J=6.4 Hz, 2H); 2.95 (s, 6H); 3.16-3.23 (m, 2H); 3.29 (q, J=7.3 Hz, 2H). LCMS (ESI$^+$, m/z): 160 [M+H]$^+$.

Anal. Calc. for C$_8$H$_{17}$NO$_2$.1.55 H$_2$O: C, 51.34; H, 10.82; N, 7.48.

Found: C, 51.36, H, 11.40, N, 7.34.

Preparation of 3-carboxy-N-ethyl-N,N-dimethylpropan-1-aminium 2-(acetyloxy)benzoate (4 a)

3-Carboxy-N-ethyl-N,N-dimethylpropan-1-aminium 2-(acetyloxy)benzoate was prepared in a form of a water mixture. Thus, ca. 90% 4-[ethyl-(dimethyl)ammonio]butanoate (3) (2.20 g, 12.44 mmol) and 2-(acetyloxy)-benzoic acid (2.266 g, 12.57 mmol) were placed in a volumetric flask and diluted with water up to 100 ml. The content of the mixture dissolves by heating and precipitates by lowering of the temperature. According to $^1$H-NMR, the precipitated solid material consists of almost pure 2-(acetyloxy)-benzoic acid.

Preparation of 3-carboxy-N-ethyl-N,N-dimethylpropan-1-aminium (2E)-3-carboxyacrylate (4 b)

To a solution of 4-[ethyl(dimethyl)ammonio]butanoate (3) (2.0 g, 12.56 mmol) in anh. ethanol (10 ml) a hot (60° C.) solution of (E)-butenedioic acid (1.46 g, 12.56 mmol) in ethanol (50 ml) was added. The reaction mixture was allowed to stand at ambient temperature for 2 h, the precipitated crystals were filtered and dried over P$_2$O$_5$ to give 2.98 g (85%) of the 3-carboxy-N-ethyl-N,N-dimethylpropan-1-aminium (2E)-3-carboxyacrylate. M.p. 122-123° C.

$^1$H-NMR (D$_2$O, DSS) δ: 1.36 (tt, J=1.9, 7.3 Hz, 3H); 2.06 (m, 2H); 2.49 (t, J=7.1 Hz, 2H); 3.06 (s, 6H); 3.31 (m, 2H); 3.40 (q, J=7.3 Hz, 2H); 6.75 (s, 1.9H, CH=CH).

LCMS ESI$^+$ (m/z): 160 [M+H]$^+$. Titration assays: water content (Fisher) 0.13%, betaine content (HClO$_4$) 93.0%, (E)-butenedioic acid content 46.1%.

Anal. Calc. for C$_8$H$_{17}$NO$_2$.1.2 C$_4$H$_4$O$_4$ (46.7%): C, 51.50, H, 7.36, N, 4.69.

Found: C, 51.52, H, 7.35, N, 4.61.

Preparation of 3-carboxy-N-ethyl-N,N-dimethylpropan-1-aminium 3-carboxypropanoate (4 c)

3-Carboxy-N-ethyl-N,N-dimethylpropan-1-aminium 3-carboxypropanoate was prepared in a form of a water solution. Thus, ca. 90% 4-[ethyl-(dimethyl)ammonio]butanoate (3) (2.20 g, 12.44 mmol) and succinic acid (1.49 g, 12.62 mmol) were placed in a volumetric flask and dissolved and diluted with water up to 100 ml.

Preparation of 3-carboxy-N-ethyl-N,N-dimethylpropan-1-aminium 2,6-dioxo-1,2,3,6-tetrahydropyrimidine-4-carboxylate (4 d)

To a solution of 4-[ethyl(dimethyl)ammonio]butanoate (3) (2.0 g, 12.56 mmol) in isopropanol (100 ml) 2,6-dioxo-1,2,3,6-tetrahydropyrimidine-4-carboxylic acid monohydrate (2.187 g, 12.56 mmol) was added and the reaction mixture was heated to reflux until all the carboxylic acid dissolved. The reaction mixture was allowed to cool to ambient temperature, the precipitated crystals were filtered, washed with isopropanol (5 ml) and diethyl ether (20 ml), and dried over P$_2$O$_5$ to give 3.238 g (97.4%) of the 3-carboxy-N-ethyl-N,N-dimethylpropan-1-aminium 2,6-dioxo-1,2,3,6-tetrahydropyrimidine-4-carboxylate. M.p. 150.7° C.

$^1$H-NMR (D$_2$O, DSS) δ: 1.36 (tt, J=2.0, 7.3 Hz, 3H); 2.05 (m, 2H); 2.47 (t, J=7.0 Hz, 2H); 3.07 (s, 6H); 3.31 (m, 2H); 3.41 (q, J=7.3 Hz, 2H); 6.20 (s, 1H, C=CH).

LCMS ESI$^+$ (m/z): 160 [M+H]$^+$.

Anal. Calc. for C$_8$H$_{17}$NO$_2$.C$_5$H$_4$N$_2$O$_4$ (49.5%): C, 49.52, H, 6.71, N, 13.33.

Found: C, 49.59, H, 6.69, N, 13.26.

Preparation of
3-carboxy-N-ethyl-N,N-dimethylpropan-1-aminium dihydrogen phosphate (4 e)

To a solution of 4-[ethyl(dimethyl)ammonio]butanoate (3) (6.4 g, 40 mmol) in water (10 ml) a solution of 85% aq. H$_3$PO$_4$ (4.73 g, 40 mmol) in acetone (10 ml) was added and the resulting solution was stirred at ambient temperature for 10 min. The reaction mixture was evaporated and azeotropically dried several times with acetone by rotary evaporator at 45° C. The obtained white crystalline substance was dried over P$_2$O$_5$ to give 9.82 g (95%) of the 3-carboxy-N-ethyl-N,N-dimethylpropan-1-aminium dihydrogen phosphate. M.p. 110-135° C.

$^1$H-NMR (D$_2$O, DSS) δ: 1.36 (tt, J=1.8, 7.3 Hz, 3H); 2.06 (m, 2H); 2.50 (t, J=7.0 Hz, 2H); 3.06 (s, 6H); 3.32 (m, 2H); 3.41 (q, J=7.3 Hz, 2H). LCMS ESI$^+$ (m/z): 160 [M+H]$^+$. Titration assays: water content (Fisher) 0.356%, betaine content (HClO$_4$)—95.682%.

Anal. Calc. for C$_8$H$_{17}$NO$_2$.0.052 H$_2$O (0.356%)·1.07 H$_3$PO$_4$ (39.6%): C, 36.26; H, 7.73; N, 5.29.

Found: C, 36.20, H, 7.72, N, 5.11.

The purity of the obtained 3-carboxy-N-ethyl-N,N-dimethylpropan-1-aminium dihydrogen phosphate was increased by crystallization from methanol. Thus, the 3-carboxy-N-ethyl-N,N-dimethylpropan-1-aminium dihydrogen phosphate (6.9 g) was crystallized from methanol (40 ml) to afford 5.326 g (77%) of the purified 3-carboxy-N-ethyl-N,N-dimethylpropan-1-aminium dihydrogen phosphate with m.p. 139° C.

Calc. for C$_8$H$_{17}$NO$_2$.H$_3$PO$_4$ (38.1%): C, 37.36; H, 7.84; N, 5.45.

Found: C, 37.52, H, 7.85, N, 5.39.

Cardioprotective Activity

Fifty male, 10 weeks old Wistar rats weighing 200-250 g were housed under standard conditions (21-23° C., 12 h light-dark cycle) with unlimited access to food (R3 diet, Lactamin AB, Sweden) and water.

Rats were adapted to local conditions for two weeks before the start of treatment. Meldonium dihydrate at a dose of 20 mg/kg, gamma-butyrobetaine at a dose of 20 mg/kg and 3-carboxy-N-ethyl-N,N-dimethylpropan-1-aminium salts at dose of 20 mg/kg were administered p.o. daily for 8 weeks. Control rats received water.

Isolated Rat Heart Infarction Study

The isolated rat heart experiment was performed essentially as described earlier (Liepinsh et al., *J. Cardiovasc. Pharmacol.* 2006; 48(6):314-9). Twenty-four hours after the last drug administration hearts were excised and retrogradely perfused via the aorta at a constant pressure with oxygenated Krebs-Henseleit buffer at 37° C. The heart rate, left ventricle end-diastolic pressure and left ventricle developed pressure were continuously recorded. Coronary flow was measured using an ultrasound flow detector (HSE) and the PowerLab 8/30 system from ADInstruments. The hearts were perfused for 20 min to stabilize the hemodynamic functions and then occlusion was performed for 60 min by constricting threads through a plastic tube. Successful occlusion was confirmed by a coronary flow decrease of about 40 percent. Reperfusion was achieved by releasing the threads. At the end of the 150-min reperfusion period, the risk zone was delineated with 0.1% methylene blue. The hearts were then sectioned transversely from the apex to the base in five slices 2 mm in thickness and incubated in 1% triphenyltetrazolium chloride in phosphate buffer (pH 7.4, 37° C.) for 10 min to stain viable tissue red and necrotic tissue white. Computerized planemetric analysis of Sony A900 photographs was performed using Image-Pro Plus 6.3 software to determine the area at risk and area of necrosis expressed as a % of the left ventricle. The obtained values were then used to calculate the infarct size (IS) as a % of risk area according to the formula:

Infarct Size=Area of Necrosis/Area at Risk×100%.

Effects in Isolated Rat Heart Infarction Model

The anti-infarction effect of examined substances was investigated in an isolated rat heart infarction model. During occlusion of left coronary artery, the coronary flow in all experimental groups was decreased for 40% (from 11 ml/min to 7 ml/min). Moreover, the drop of developed left ventricular pressure for 50% was observed. The heart rate during the occlusion period did not change significantly. In reperfusion stage, coronary flow, developed left ventricular pressure, ±dp/dt values were recovered till about 80% of control level. There were no significant differences between control and treatment groups.

Effects of Meldonium dihydrate (20 mg/kg), gamma-butyrobetaine (20 mg/kg) and 3-carboxy-N-ethyl-N,N-dimethylpropan-1-aminium salts (20 mg/kg) after 2 weeks of treatment on infarct size in the isolated rat heart infarction experiment are presented in Table 1, Table 2, Table 3, Table 4, Table 5, Table 6

TABLE 1

| | Infarct size, % of control |
|---|---|
| Control | 100.0 ± 5.9 |
| Meldonium dihydrate 20 mg/kg | 117.9 ± 7.9 |
| Gamma-butyrobetaine 20 mg/kg | 87.6 ± 11.4 |
| 3-Carboxy-N-ethyl-N,N-dimethylpropan-1-aminium 2-(acetyloxy)benzoate 20 mg/kg | 61.6 ± 6.7*,#,$ |

Effects of Meldonium dihydrate, gamma-butyrobetaine and 3-carboxy-N-ethyl-N,N-dimethylpropan-1-aminium 2-(acetyloxy)benzoate on infarct size

TABLE 2

| | Infarct size, % of control |
|---|---|
| Control | 100.0 ± 5.9 |
| Meldonium dihydrate 20 mg/kg | 117.9 ± 7.9 |
| Gamma-butyrobetaine 20 mg/kg | 87.6 ± 11.4 |
| 3-carboxy-N-ethyl-N,N-dimethylpropan-1-aminium (2E)-3-carboxyacrylate 20 mg/kg | 46.5 ± 7.0*,#,$ |

Effects of Meldonium dihydrate, gamma-butyrobetaine and 3-carboxy-N-ethyl-N,N-dimethylpropan-1-aminium (2E)-3-carboxyacrylate on infarct size

TABLE 3

| | Infarct size, % of control |
|---|---|
| Control | 100.0 ± 5.9 |
| Meldonium dihydrate 20 mg/kg | 117.9 ± 7.9 |

TABLE 3-continued

| | Infarct size, % of control |
|---|---|
| Gamma-butyrobetaine 20 mg/kg | 87.6 ± 11.4 |
| 3-carboxy-N-ethyl-N,N-dimethylpropan-1-aminium 2,6-dioxo-1,2,3,6-tetrahydropyrimidine-4-carboxylate 20 mg/kg | 60.6 ± 6.7*,#,$ |

Effects of Meldonium dihydrate, gamma-butyrobetaine and 3-carboxy-N-ethyl-N,N-dimethylpropan-1-aminium 2,6-dioxo-1,2,3,6-tetrahydropyrimidine-4-carboxylate on infarct size

TABLE 4

| | Infarct size, % of control |
|---|---|
| Control | 100.0 ± 5.9 |
| Meldonium dihydrate 20 mg/kg | 117.9 ± 7.9 |
| Gamma-butyrobetaine 20 mg/kg | 87.6 ± 11.4 |
| 3-carboxy-N-ethyl-N,N-dimethylpropan-1-aminium dihydrogen phosphate 20 mg/kg | 56.1 ± 4.4*,#,$ |

Effects of Meldonium dihydrate, gamma-butyrobetaine and 3-carboxy-N-ethyl-N,N-dimethylpropan-1-aminium dihydrogen phosphate on infarct size

TABLE 5

| | Infarct size, % of control |
|---|---|
| Control | 100.0 ± 5.9 |
| Meldonium dihydrate 20 mg/kg | 117.9 ± 7.9 |
| Gamma-butyrobetaine 20 mg/kg | 87.6 ± 11.4 |
| 3-carboxy-N-ethyl-N,N-dimethylpropan-1-aminium 3-carboxypropanoate 20 mg/kg | 62.9 ± 4.7*,#,$ |

Effects of Meldonium dihydrate, gamma-butyrobetaine and 3-carboxy-N-ethyl-N,N-dimethylpropan-1-aminium 3-carboxypropanoate on infarct size Each values in mentioned Tables from 1-5 represents the mean±s.e.m. of 9-10 animals.
*p<0.05 compared with control group; #p<0.05 compared with Gamma-butyrobetaine group, $p<0.05 compared with Meldonium dihydrate group As it is presented in Tables 1-5, Meldonium dihydrate treatment at a dose of 20 mg/kg had no therapeutical effect; gamma-butyrobetaine has decreased infarct size by 12.4%.

3-Carboxy-N-ethyl-N,N-dimethylpropan-1-aminium 2-(acetyloxy)benzoate at dose of 20 mg/kg decreased infarction size by 38.4%.

3-Carboxy-N-ethyl-N,N-dimethylpropan-1-aminium (2E)-3-carboxyacrylate at dose of 20 mg/kg decreased infarction size by 53.5%.

3-Carboxy-N-ethyl-N,N-dimethylpropan-1-aminium 2,6-dioxo-1,2,3,6-tetrahydropyrimidine-4-carboxylate at dose of 20 mg/kg decreased infarction size by 39.4%.

3-Carboxy-N-ethyl-N,N-dimethylpropan-1-aminium dihydrogen phosphate at dose of 20 mg/kg decreased infarction size by 43.9%.

3-Carboxy-N-ethyl-N,N-dimethylpropan-1-aminium 3-carboxypropanoate at dose of 20 mg/kg decreased infarction size by 37.1%.

The invention claimed is:

1. 3-Carboxy-N-ethyl-N,N-dimethylpropan-1-aminium dihydrogen phosphate

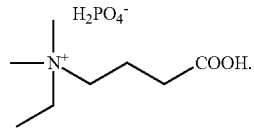

2. A process for preparing the 3-carboxy-N-ethyl-N,N-dimethylpropan-1-aminium dihydrogen phosphate according to claim 1, comprising:
   a. adding N,N-dimethylethylamine to ethyl 4-bromobutanoate in appropriate solvent to obtain 4-ethoxy-N-ethyl-N,N-dimethyl-4-oxo-1-butanaminium bromide;
   b. passing 4-ethoxy-N-ethyl-N,N-dimethyl-4-oxo-1-butanaminium bromide through ion exchange resin column to obtain 4-[ethyl(dimethyl)ammonio] butanoate;
   c. adding phosphoric acid in appropriate solvent to obtain the 3-carboxy-N-ethyl-N,N-dimethylpropan-1-aminium dihydrogen phosphate.

3. The process according to claim 2, wherein in step a) the appropriate solvent is acetonitrile or acetone.

4. A method for treating a cardiovascular disease in a subject in need thereof, comprising administration of an effective amount of the 3-carboxy-N-ethyl-N,N-dimethylpropan-1-aminium salt dihydrogen phosphate of claim 1, wherein the cardiovascular disease is ischemic heart disease or myocardial infarction.

5. The method according to claim 4, wherein the cardiovascular disease is ischemic heart disease.

6. The method according to claim 4, wherein the cardiovascular disease is myocardial infarction.

* * * * *